(12) United States Patent
Yoo

(10) Patent No.: US 11,969,287 B2
(45) Date of Patent: Apr. 30, 2024

(54) ARTIFICIAL INTELLIGENCE ULTRASOUND-MEDICAL-DIAGNOSIS APPARATUS USING SEMANTIC SEGMENTATION AND REMOTE MEDICAL-DIAGNOSIS METHOD USING THE SAME

(71) Applicant: Research & Business Foundation Sungkyunkwan University, Suwon-si (KR)

(72) Inventor: Jae-Chern Yoo, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 475 days.

(21) Appl. No.: 16/927,118

(22) Filed: Jul. 13, 2020

(65) Prior Publication Data
US 2021/0224991 A1 Jul. 22, 2021

(30) Foreign Application Priority Data
Jan. 17, 2020 (KR) .................. 10-2020-0006272

(51) Int. Cl.
*A61B 8/08* (2006.01)
*A61B 8/00* (2006.01)
(Continued)

(52) U.S. Cl.
CPC ............ *A61B 8/085* (2013.01); *A61B 8/0825* (2013.01); *A61B 8/0866* (2013.01); *A61B 8/0875* (2013.01); *A61B 8/0883* (2013.01); *A61B 8/0891* (2013.01); *A61B 8/4472* (2013.01); *A61B 8/463* (2013.01); *A61B 8/467* (2013.01); *A61B 8/488* (2013.01); *G06N 3/08* (2013.01); *G06T 7/0014* (2013.01); *G06T 7/11* (2017.01); *G06T 7/13* (2017.01); *G06T 7/70* (2017.01); *G06V 10/25* (2022.01); *G06V 10/44* (2022.01);
(Continued)

(58) Field of Classification Search
CPC . G06T 7/0014; G06T 7/13; G06T 7/11; G06T 2207/20081; G06T 2207/20084
See application file for complete search history.

(56) References Cited

U.S. PATENT DOCUMENTS

| 10,825,168 B2 * | 11/2020 | Tegzes ................. G06T 7/0012 |
| 2005/0096539 A1 * | 5/2005 | Leibig ...................... A61B 8/00 600/453 |

(Continued)

FOREIGN PATENT DOCUMENTS

| EP | 2 140 412 B1 | 12/2018 |
| EP | 2140412 B1 * | 12/2018 | ............. G06F 19/00 |
| EP | 3453336 B1 * | 11/2020 | ............... A61B 8/08 |

*Primary Examiner* — Ashley K Buran
*Assistant Examiner* — Aminah Asghar
(74) *Attorney, Agent, or Firm* — NSIP Law

(57) ABSTRACT

Provided are an artificial intelligence ultrasound-medical-diagnosis apparatus and a remote medical-diagnosis method using the same. The apparatus can automatically diagnose diseases based on ultrasound medical examinations and ultrasound image processing. The ultrasound-medical-diagnosis apparatus includes a semantic segmentation artificial intelligence network configured to perform labeling on visualized organs of a patient using mutually different colors to detect a position of an organ of interest displayed on the ultrasound image.

13 Claims, 5 Drawing Sheets

(51) Int. Cl.
*G06N 3/08* (2023.01)
*G06T 7/00* (2017.01)
*G06T 7/11* (2017.01)
*G06T 7/13* (2017.01)
*G06T 7/70* (2017.01)
*G06V 10/25* (2022.01)
*G06V 10/44* (2022.01)
*G06V 10/82* (2022.01)
*G06V 30/262* (2022.01)

(52) U.S. Cl.
CPC ............ *G06V 10/82* (2022.01); *G06V 30/274* (2022.01); *G06T 2207/10132* (2013.01); *G06T 2207/20081* (2013.01); *G06T 2207/20084* (2013.01)

(56) References Cited

U.S. PATENT DOCUMENTS

| | | | |
|---|---|---|---|
| 2019/0125306 A1* | 5/2019 | Oh | G16H 50/20 |
| 2019/0148011 A1* | 5/2019 | Rao | A61B 8/5292 |
| | | | 600/437 |
| 2021/0166396 A1* | 6/2021 | Chen | G06V 20/40 |

* cited by examiner

[FIG. 1]
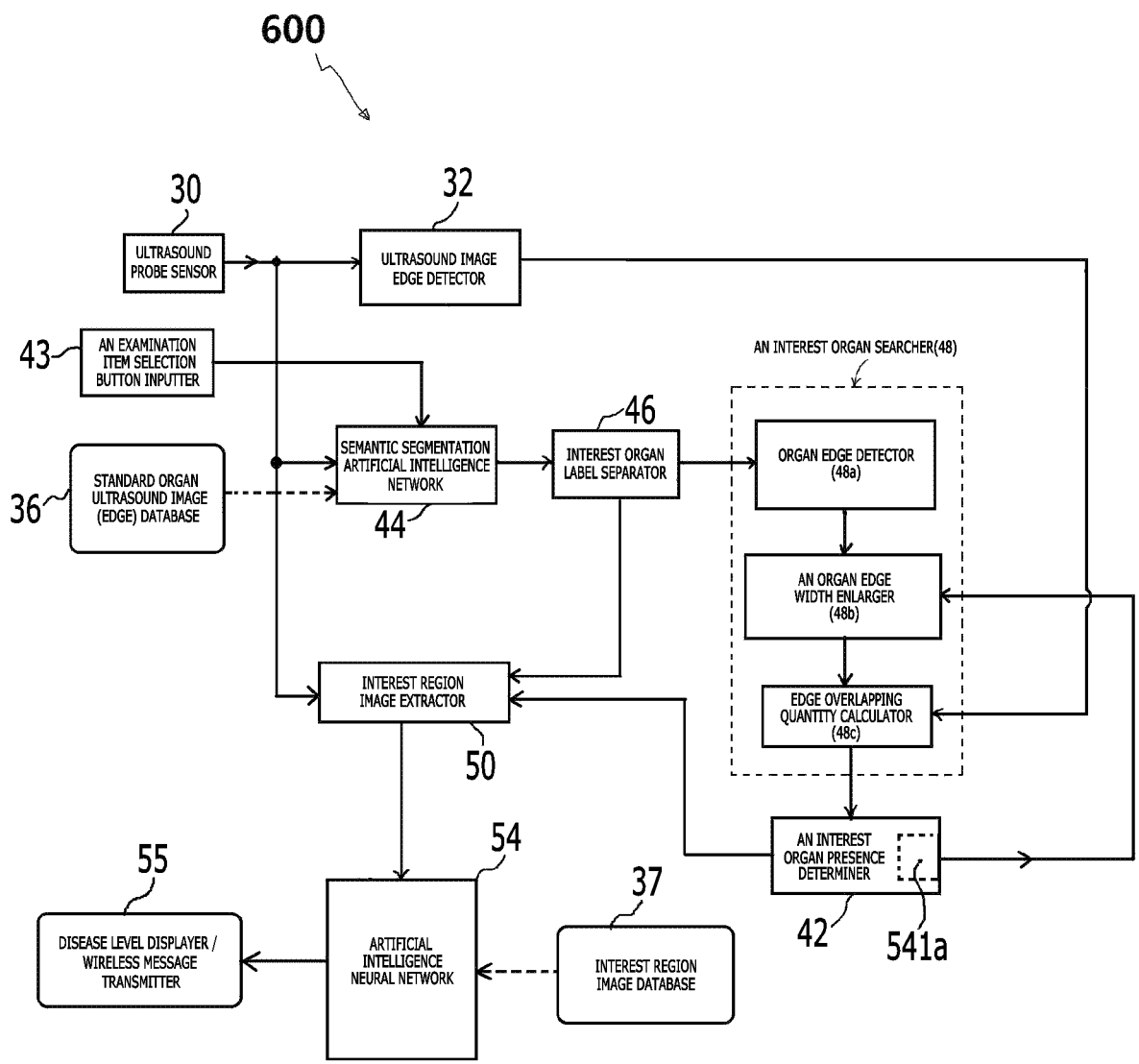

[FIG. 2(a)]
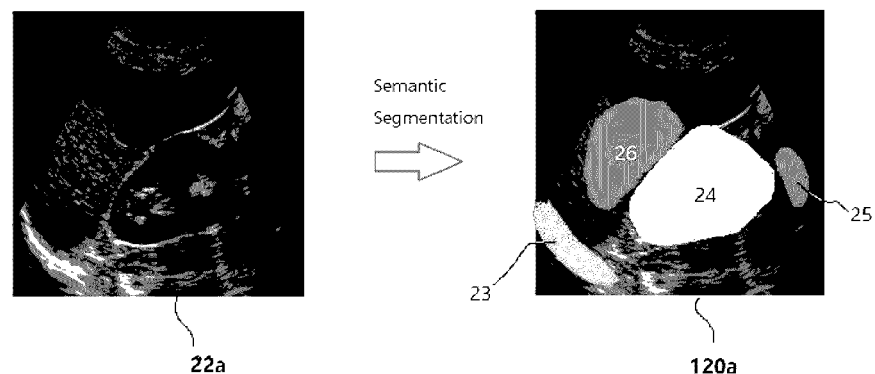
[FIG. 2(b)]
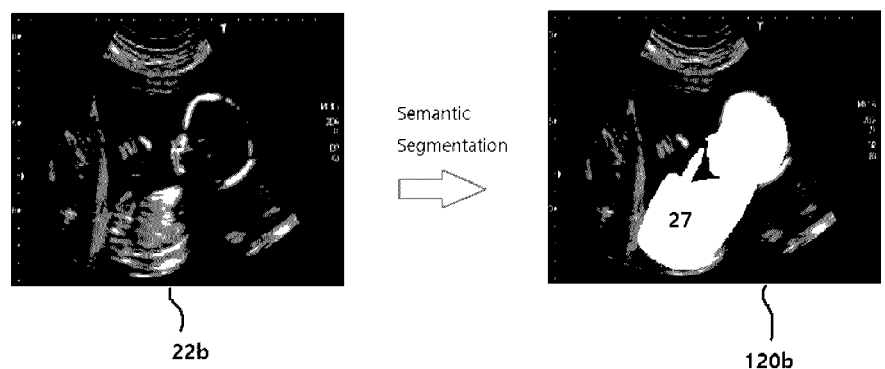

[FIG. 3]
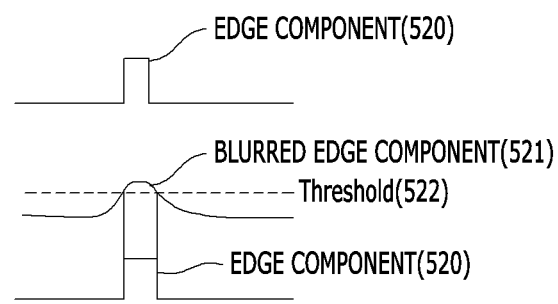
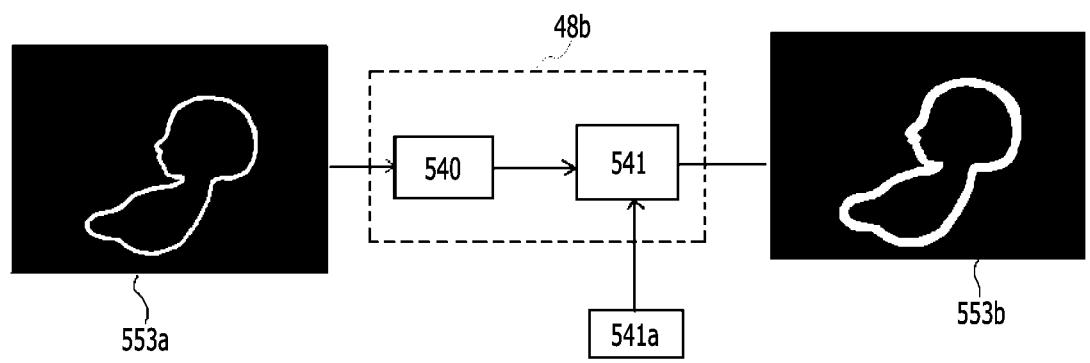

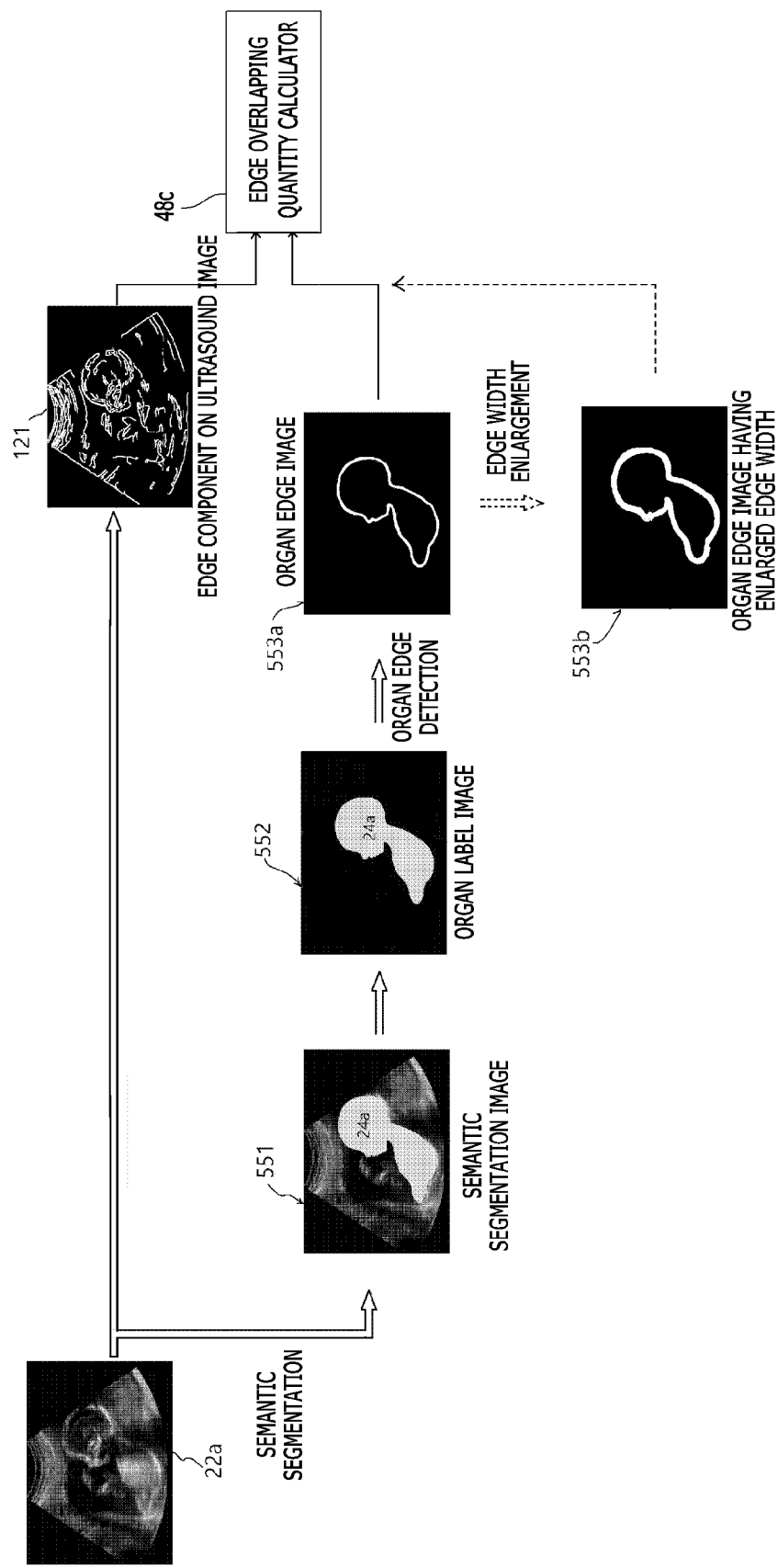

[FIG.5]
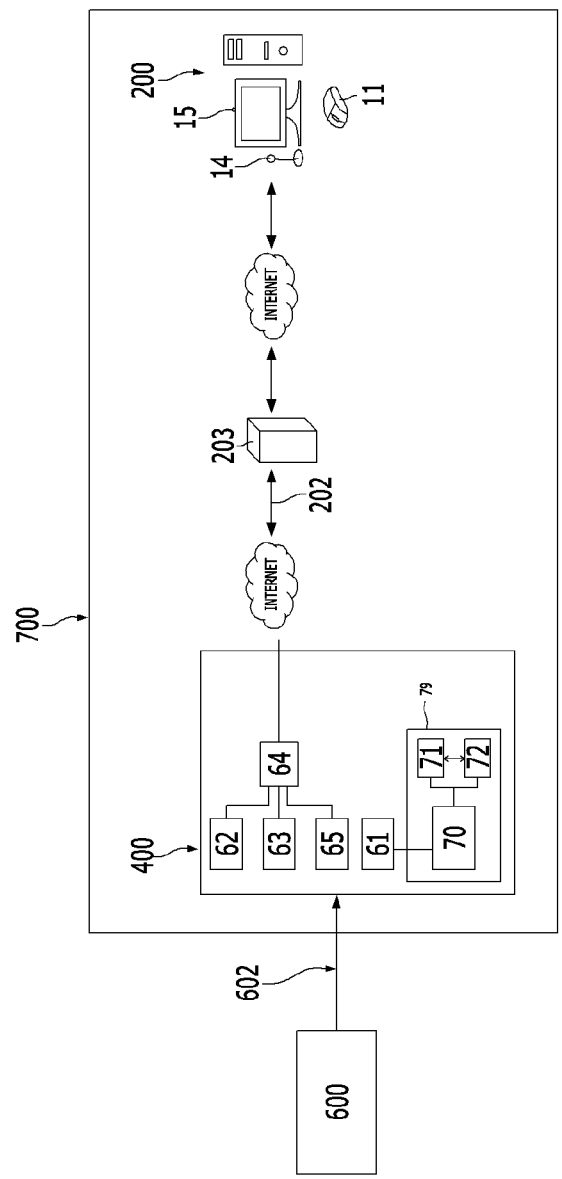
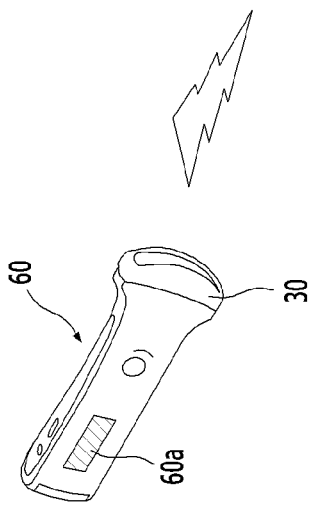

ARTIFICIAL INTELLIGENCE ULTRASOUND-MEDICAL-DIAGNOSIS APPARATUS USING SEMANTIC SEGMENTATION AND REMOTE MEDICAL-DIAGNOSIS METHOD USING THE SAME

CROSS-REFERENCE TO RELATED APPLICATIONS

This application claims the benefit under 35 USC 119(e) of Korean Patent Application No. 10-2020-0006272 filed on Jan. 17, 2020, in the Korean Intellectual Property Office, the entire disclosure of which is incorporated herein by reference for all purposes.

BACKGROUND

1. Field

The present disclosure relates to an artificial intelligence ultrasound-medical-diagnosis apparatus using semantic segmentation and a remote medical-diagnosis method using the same.

2. Description of the Related Art

The pre-applied invention provides a remote medical-diagnosis system and a remote medical-diagnosis method using the same. The system includes a bio-analysis apparatus including a bio-disc or a lab on a disc which receives a sample to perform a biological, chemical, or biochemical reaction; a virtual doctor which includes medical treatment equipment such as a thermometer useable for medical treatment, a blood pressure monitor, a camera, a stethoscope, a body fat meter, an arteriosclerosis diagnosis device, an ultrasound image diagnosis device, a urine examination device, a pulse rater, a blood collection device, an electrocardiogram, an X-Ray device, an oxygen saturation examination device, a dementia examination device, a computerized axial tomography (CAT) device, a magnetic resonance imaging (MRI) device, a capsule endoscope, a magnifier, a camera-integrated magnifier, a medical measurement instrument, a biological signal detection device, and a bio shirt provided with a function to measure biological signals (diabetes, obesity, blood pressure, pulse, electrocardiogram, and body temperature), and which is resident on a user terminal in a software form so as to guide or instruct a method of using the bio-analysis apparatus and the medical treatment equipment, and which provides a consulting service exchanged with a user; a user terminal which provides a consulting service exchanged with a medical professional or the virtual doctor; a medical professional terminal which provides a consulting service exchanged with a user; and a remote diagnosis server as a consulting professional, which connects the medical professional to the user during a regular check-up period, which connects the virtual doctor to the user during other periods, and which disconnects the consulting service between the user and the virtual doctor after the lapse of the regular check-up period during which the user needs the consulting service from the medical professional.

Recently, a digital image processing technology has been applied to a clinical diagnosis field along with a medical equipment manufacturing technology, and imaging medicine has been considerably developed.

In particular, ultrasound diagnosis is not harmful to a human body since harmful radiation exposure can be avoided compared to CT or X-ray medical equipment. The ultrasound-diagnosis apparatus can obtain a cross-sectional image of the human body by using a non-invasive method, and has characteristics of convenient carriage and low cost. In particular, it is possible to obtain an image on a real-time basis. Therefore, there is an advantage in that a movement state of an organ can be observed on a real-time basis.

However, due to characteristics of low resolution and severe noise of an ultrasound image, a critical calculation error occurs, and the ultrasound image is severely damaged. Therefore, in many cases, even a professional is less likely to accurately and medically interpret the ultrasound image.

The present application is made to solve the above-described problems in the related art, and aims to provide an artificial intelligence ultrasound-medical-diagnosis apparatus using semantic segmentation which adopts an artificial intelligence neural network subjected to deep learning in advance by a database including interest region images of interest organs including ultrasound images labeled for each disease level, and a semantic segmentation artificial intelligence network for obtaining organ label images labeled with mutually different colors for interest organs from the ultrasound image.

The present application is made to solve the above-described problems in the related art, and provides an artificial intelligence ultrasound-medical-diagnosis apparatus using semantic segmentation and a remote medical-diagnosis method using the same, in which an organ edge image indicating an edge component of the organ label image from the organ label image, in which a position of the interest organ is subsequently detected on the ultrasound image by using the number of overlapping edge pixels between the edge component of the organ edge image and the edge component of the ultrasound image, and in which an artificial intelligence neural network subjected to deep learning in advance is used to automatically determine a diseases type and a disease level of a patient, based on the ultrasound image of the patient which is input from an ultrasound image sensor.

However, technical tasks to be achieved by embodiments of the present application are not limited to technical tasks as described above, and other technical tasks may exist.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an ultrasound-medical-diagnosis apparatus using semantic segmentation, includes: an ultrasound probe sensor configured to acquire an ultrasound image from a patient; an ultrasound image edge detector configured to detect a plurality of edge components on the ultrasound image; an ultrasound examination item selection button inputter configured to select an organ of interest of the patient; a semantic segmentation artificial intelligence network configured to perform labeling on each of a plurality of organs of the patient using mutually different colors to detect a position of the organ of interest from the ultrasound image; an interest organ label separator configured to generate an organ label image displayed by extracting and separating the organ of interest out of the plurality of organs; an interest organ searcher including an organ edge detector configured to generate an organ edge image by detecting an edge component of the organ label image, an organ edge width enlarger configured to generate the organ edge image obtained by enlarging an edge width of the edge component detected by the organ edge detector, and an edge overlapping quantity calculator configured to calculate a number of overlapping edge pixels overlapped by comparing the edge component on the organ edge image and the edge component on the ultrasound image with each other on two-dimensional spatial coordinates; an interest organ presence determiner configured to determine whether the organ of interest is present on the ultrasound image using the number of overlapping edge pixels calculated from the interest organ searcher; an interest region image extractor configured to extract an interest region image through space addressing on the ultrasound image for an organ of interest region or an ultrasound-medical-diagnosis interest region around the organ of interest region, upon the organ of interest being present on the ultrasound image; and a disease level displayer configured to determine and display a disease type and a disease level of the organ of interest based on the interest region image.

The semantic segmentation artificial intelligence network may be deep-learning trained in advance based on a standard organ ultrasound image database including a labeled standard organ ultrasound image.

The apparatus may further include an interest region image database including the ultrasound images labeled for each disease type and each disease level for the organ of interest inside a human body.

The apparatus may further include a wireless message transmitter configured to transmit the disease level information to a mobile device of the patient in a form of a wireless message.

The interest organ presence determiner may further include an edge width adjuster configured to transmit a feedback signal for enlarging the edge width to the organ edge width enlarger.

The semantic segmentation artificial intelligence network may include an artificial intelligence neural network configured to perform the semantic segmentation on main organs corresponding to the ultrasound images, after learning is performed by the ultrasound images labeled using mutually different colors for each organ, on the main organs involved in any one examination selected from a fetal examination, a carotid artery examination, a breast cancer examination, an appendix (appendicitis) examination, a prostate ultrasound examination, and ultrasound examinations based on human organs including a liver, a heart, a joint, a spine, a uterus, a gallbladder, a genital, a bile duct, a pancreas, a spleen, and a kidney, a thyroid tumor examination, and a vascular Doppler ultrasound examination.

In another general aspect, an artificial intelligence ultrasound-medical-diagnosis apparatus using semantic segmentation, includes a remote medical-diagnosis system, comprising ultrasound-medical equipment having an ultrasound probe sensor; a wireless transmitter integrated into the ultrasound-medical equipment to transmit medical image data of a patient measured by the ultrasound-medical equipment, wherein the apparatus is configured to measure a disease level by receiving an ultrasound image of the patient transmitted from the wireless transmitter; a user terminal comprising a camera configured to monitor the ultrasound-medical equipment, a first authenticator configured to wirelessly authenticate a product ID of the ultrasound-medical equipment, a recorder configured to store the ultrasound image, an Internet connector configured to transmit the ultrasound image and the product ID of the ultrasound-medical equipment to a remote diagnosis server, and a first consulting servicer configured to provide a consulting service exchanged with a medical professional; an artificial intelligence neural network resident on the user terminal and configured to perform deep learning using a medical image database accumulated by the ultrasound-medical equipment; a virtual doctor including a guide member resident on the user terminal and configured to guide or instruct a method of using the ultrasound-medical equipment, and a diagnosis member configured to output a diagnosis result by causing an artificial intelligence neural network subjected to the deep learning in advance to automatically diagnose medical image data obtained from the patient by the ultrasound-medical equipment; and a medical professional terminal including a receptor configured to receive the medical image data or the ultrasound image through the communication network, and a second consulting servicer configured to provide a consulting service exchanged between a user and a medical professional.

The apparatus may further include a communication interface configured to provide a connection between the artificial intelligence ultrasound-medical-diagnosis apparatus and the user terminal.

The method of using the ultrasound-medical equipment may include extracting an edge component of the ultrasound image; acquiring a semantic segmentation image by causing a semantic segmentation artificial intelligence network to perform semantic segmentation on the ultrasound image; forming an organ label image by extracting an interest organ region from the semantic segmentation image; causing an organ edge detector to acquire an organ edge image indicating an edge component of the organ label image; comparing the edge component on the organ edge image and the edge component on the ultrasound image with each other on two-dimensional spatial coordinates, and recognizing a position of an interest organ on the ultrasound image by calculating the number of overlapping edge pixels; including an ultrasound-medical-diagnosis interest region around the extracted organ of interest region, on an interest region image; outputting a diagnosis result by causing an artificial intelligence neural network subjected to deep learning in advance to automatically analyze the interest region image obtained from a virtual doctor; and performing a remote consulting service exchanged with a medical professional, based on the diagnosis result.

Other features and aspects will be apparent from the following detailed description, the drawings, and the claims.

BRIEF DESCRIPTION OF THE DRAWINGS

FIG. 1 illustrates an embodiment of an artificial intelligence ultrasound-medical-diagnosis apparatus using semantic segmentation, according to an embodiment of the present disclosure.

FIGS. 2(a) and 2(b) illustrate an embodiment in which the semantic segmentation is performed on an ultrasound image by a semantic segmentation artificial intelligence network according to an embodiment of the present disclosure, and illustrates an embodiment of the ultrasound image labeled using mutually different colors for each organ.

FIG. 3 illustrates an embodiment of an organ edge width enlarger that enlarges a width of an edge component detected by an organ edge detector, according to an embodiment of the present disclosure, on a two-dimensional space so as to generate the edge component having an enlarged edge width.

FIG. 4 illustrates an embodiment of a process for detecting a position of a fetus on an ultrasound image by comparing the edge component on an organ edge image and the edge component on the ultrasound image with each other on a two-dimensional space and by calculating the number of overlapping edge pixels in order to detect the position of the fetus inside a uterus serving as one of interest organs from the ultrasound image, according to an embodiment of the present disclosure.

FIG. 5 illustrates an embodiment in which the artificial intelligence ultrasound-medical-diagnosis apparatus, according to the embodiment of the present disclosure, is connected to an artificial intelligence virtual doctor resident in a remote medical-diagnosis system so as to automatically analyze and diagnose ultrasound medical image data of a patient.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION OF THE EMBODIMENT

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

The features of the examples described herein may be combined in various ways as will be apparent after an understanding of the disclosure of this application. Further, although the examples described herein have a variety of configurations, other configurations are possible as will be apparent after an understanding of the disclosure of this application.

The present disclosure relates to an artificial intelligence ultrasound-medical-diagnosis apparatus using semantic segmentation and a remote medical-diagnosis method using the same, which can automatically determine various diseases from ultrasound images acquired through imaging medical examinations. A position of an organ of interest is detected on an ultrasound image by calculating the number of overlapping edge pixels between an edge component of an organ edge image and an edge component of the ultrasound image which are obtained based on a result of the semantic segmentation from the ultrasound image, and in which a disease type and a disease level of a patient can be automatically determined based on the ultrasound image of the patient which is input from an ultrasound image sensor by using an artificial intelligence neural network subjected to deep learning in advance by an interest region image database including ultrasound images labeled for each disease level.

In addition, the artificial intelligence ultrasound-medical-diagnosis apparatus according to the present disclosure is advantageously used for implementation of a virtual doctor which automatically analyzes a diseases type and a disease level of a patient, informs the patient or a doctor of an analysis result, and provides a consulting service remotely through the Internet.

FIG. 1 illustrates an embodiment of an artificial intelligence ultrasound-medical-diagnosis apparatus 600 using semantic segmentation, according to the embodiment of the present disclosure.

The artificial intelligence ultrasound-medical-diagnosis apparatus 600 using the semantic segmentation may include an ultrasound probe sensor 30, an ultrasound image edge detector 32, a standard organ ultrasound image database 36, an interest region image database 37, an interest organ presence determiner 42, an examination item selection button inputter 43, a semantic segmentation artificial intelligence network 44, an interest organ label separator 46, an interest organ searcher 48, an interest region image extractor 50, an artificial intelligence neural network 54, a disease level displayer, and a wireless message transmitter 55.

According to the embodiment of the present disclosure, the ultrasound probe sensor 30 may acquire an ultrasound image from a patient.

In addition, the ultrasound image edge detector 32 may detect edge components on the ultrasound image. The ultrasound image edge detector 32 may extract the edge components on the ultrasound image.

In addition, the ultrasound examination item selection button inputter 43 may select a diagnosis target interest organ inside a body. The ultrasound examination item selection button inputter 43 may receive an input for selecting at least one of a plurality of diagnosis target interest organs inside the body, from a user.

In addition, the standard organ ultrasound image database 36 may store a standard organ ultrasound image labeled using mutually different colors for each organ in order to detect and recognize a position of the interest organ inside the body from the ultrasound image. The artificial intelligence network 44 may perform deep learning, based on the standard organ ultrasound image stored in the standard organ ultrasound image database 36.

In addition, the interest organ label separator 46 may generate an organ label image displayed by extracting and separating only the interest organ corresponding to an examination item selected by a user via the ultrasound examination item selection button inputter 43, out of organs subjected to semantic segmentation by the semantic segmentation artificial intelligence network 44 from the ultrasound image.

According to an embodiment of the present disclosure, the interest organ searcher 48 may include an organ edge detector 48a, an organ edge width enlarger 48b, and an edge overlapping quantity calculator 48c.

In addition, the organ edge detector 48a may detect the edge component of the organ label image to generate an organ edge image.

If necessary, the organ edge width enlarger 48b may generate the organ edge image having an enlarged edge width to be larger than the edge component obtained from the organ edge detector 48a.

The edge overlapping quantity calculator 48c may calculate the number of overlapping edge pixels by comparing the edge component on the detected organ edge image and the edge component on the ultrasound image in a two-dimensional space.

The interest organ presence determiner 42 may determine the presence or absence of the interest organ on the ultrasound image by using the number of overlapping edge pixels which is calculated from the interest organ searcher 48.

In a case where the interest organ is present on the ultrasound image, the interest region image extractor 50 may extract the interest organ from the ultrasound image through space addressing of the interest organ within the ultrasound image to identify an interest organ region or a whole medically associated ultrasound-medical-diagnosis interest region around the interest organ region.

In addition, the interest region image database 37 may include ultrasound images that are each labeled with disease type and disease level for specific organs inside the body.

According to the embodiment of the present disclosure, the artificial intelligence ultrasound-medical-diagnosis apparatus 600 using the semantic segmentation includes the artificial intelligence neural network 54 subjected to deep learning in advance by the interest region image database 37. The artificial intelligence ultrasound-medical-diagnosis apparatus 600 includes a disease level displayer that causes the artificial intelligence neural network 54 to automatically determine and display a disease type and a disease level of the interest organ of a patient by using the interest region image extracted from the ultrasound image of the patient which is input from the ultrasound probe sensor 30, or the wireless message transmitter 55 that transmits disease level information to a mobile device of the patient in a form of a wireless message.

In a case where the number of overlapping edge pixels is equal to or greater than a predetermined numerical value, the interest organ presence determiner 42 determines that the interest organ is present on the ultrasound image, and that the organ label image displays a position of the corresponding interest organ by using a color label.

According to the embodiment of the present disclosure, in a case where the interest organ is present on the ultrasound image, the interest region image extractor 50 may extract the interest organ through space addressing on the ultrasound image for the ultrasound-medical-diagnosis interest region associated with a geometric position around the interest organ region.

For example, in a case where a liver disease is selected as the examination item, it is desired for the diagnosis of the liver disease to obtain the ultrasound image on a parasagittal scan plane included in a liver and a kidney from the ultrasound image. However, due to ambiguity of image quality, it is difficult to directly identify a liver region on the ultrasound image.

However, owing to a clear shape of the kidney, it is easier to identify a kidney region on the ultrasound image. Therefore, in a case where a fatty liver is selected as the examination item, the interest organ is the kidney. The interest region image extractor 50 may extract an image of the liver region from the ultrasound image through geometric position measurement, in view of a relative distance and an arrangement situation of a medical body organ around the kidney identified by the interest organ searcher 48.

Therefore, when the liver disease is diagnosed, the disease type and the disease level may be automatically determined in the following manner. The artificial intelligence neural network 54 is subjected to learning in advance by extracting the image of the liver region in addition to the image of the kidney region and including the extracted images in the interest region image. Similarly, the image of the liver region in addition to the image of the kidney region from the ultrasound image of the patient which is input by the ultrasound probe sensor is included in the interest region image.

According to the present disclosure, in an example, a size of the ultrasound image region obtained by the interest region image extractor 50 varies depending on the examination item. For example, in a case where a fatty liver examination is designated as the examination item, in an example, the ultrasound image region obtained by the interest region image extractor 50 includes the whole liver and kidney regions.

According to the present disclosure, in an example, the standard organ ultrasound image database 36 includes the ultrasound image of a normal person who has no disease around the interest organ.

As the examination item selection button inputter 43 for selecting the interest organ, it is desirable to use a touch screen. Desirably, the ultrasound examination items are listed and displayed on the touch screen, and the examination (diagnosis) item is selected by a touch operation of the user. Subsequently, the interest organ is automatically registered. In an example, the semantic segmentation artificial intelligence network 44 performs the semantic segmentation on the ultrasound image around the automatically registered interest organ.

According to the present disclosure, in an example, the interest region image database 37 for the learning of the artificial intelligence neural network 54 includes the ultrasound images labeled by the disease type and the diseases level for each ultrasound examination item.

The disease type and the disease level are determined depending on the diagnosis items. For example, in a case where the liver is designated as the examination item, the disease type may be classified into the fatty liver or the liver cancer. The disease level may be classified into mild, moderate, severe, and liver cirrhosis levels.

In a case where it is ambiguous for the interest organ presence determiner 42 to determine whether the interest organ is included on the ultrasound image, various variations in semantic segmentation capability of the semantic segmentation artificial intelligence network 44 are considered. In this manner, it is desirable to reconfirm the presence of the organ by enlarging the edge width of the organ label image as much as a prescribed amount. In this case, in an example, the interest organ presence determiner 42 further includes an edge width adjuster 541a for transmitting a feedback signal for enlarging the edge width to the organ edge width enlarger 48b.

The organ edge width enlarger 48b causes the edge overlapping quantity calculator 48c to compare the edge component on the organ edge image and the edge component on the ultrasound image with each other on two-dimensional spatial coordinates. While the edge overlapping quantity calculator 48c calculates the number of overlapping edge pixels, due to various variations in the semantic segmentation capability of the semantic segmentation artificial intelligence network 44, in an example, the organ edge width enlarger 48b receives the feedback signal from the edge width adjuster 541a so that a threshold for enlarging the edge width is adjusted to prevent or mitigate missing of the overlapping edge pixels.

According to the present disclosure, in an example, an edge width enlargement ratio of the organ edge width enlarger 48b to reconfirm the presence of the organ is set to twice.

According to the present disclosure, extracting the edge component may be a method of detecting and processing an outline of an image object or a boundary line of a region. In a portion of the outline or the boundary line of the image, an intensity value of the image is rapidly changed. The rapidly changed portion of the intensity value is called an edge or a rim. According to present disclosure, in detecting the edge component, it is desirable to select and use any one of Sobel, Prewitt, Laplacian, Roberts, and Kenny edge detection techniques.

The ultrasound image edge detector (edge detector) detects the edge components on the ultrasound image.

According to the present disclosure, as the artificial intelligence neural network, it is desirable to use a convolutional neural network (CNN) and a recurrent neural network (RNN).

According to the present disclosure, the artificial intelligence neural network is a neural network that allows deep learning, and includes a combination of any one or more layers or elements selected from a convolution layer, a pooling layer, a ReLu layer, a transpose convolution layer, an unpooling layer, a 1×1 convolution layer, skip connection, a global average pooling (GAP) layer, a fully connected layer, a support vector machine (SVM), a long short term memory (LSTM), Atrous convolution, Atrous spatial pyramid pooling, separable convolution, and bilinear upsampling. In an example, the artificial intelligence neural network further includes a calculator for calculating batch normalization in a front stage of the ReLu layer.

According to the present disclosure, in a case where the interest organ is present on the ultrasound image, in order to confirm the position of the interest organ, the semantic segmentation artificial intelligence network 44 is an artificial intelligence network classifying the interest organs in units of pixels and performing the segmentation from other objects. In this manner, in an example, the semantic segmentation artificial intelligence network 44 is subjected to learning in advance by the standard organ ultrasound image database 36 labeled using mutually different colors for each interest organ.

FIG. 2 (a) illustrates an embodiment in which the semantic segmentation is performed on an ultrasound image 22a on a parasagittal scan plane by the semantic segmentation artificial intelligence network 44, and illustrates an embodiment of an ultrasound image 120a on which the semantic segmentation is performed using mutually different colors for each organ.

The reference numeral 26 represents a liver, the reference numeral 25 represents a spleen, the reference numeral 24 represents a kidney, and the reference numeral 23 represents a diaphragm, which indicate organ regions on which the semantic segmentation is performed.

FIG. 2 (b) illustrates an embodiment in which the semantic segmentation is performed on a fetal ultrasound image 22b by the semantic segmentation artificial intelligence network 44, and illustrates an embodiment of an ultrasound image 120b obtained by performing the semantic segmentation on a fetus.

The reference numeral 27 indicates that the semantic segmentation is performed on a fetal region inside a uterus.

Desirably, according to another embodiment of the semantic segmentation artificial intelligence network 44 is subjected to learning through the ultrasound images labeled using mutually different colors for each of main organs involved in a fetal examination, a carotid artery examination, a breast cancer examination, an appendix (appendicitis) examination, a prostate ultrasound examination, ultrasound examinations for human organs including a joint, a spine, a liver, a gallbladder, a bile duct, a pancreas, a spleen, and a kidney, a thyroid tumor examination, and a vascular Doppler ultrasound examination. Thereafter, it is desirable to perform the semantic segmentation on the ultrasound images for the main organs.

According to the present disclosure, in an example, the interest organ is any one or more organs selected from the heart, the liver, the genitals, the kidney, the spleen, the diaphragm, the breast, the uterus, the fetus, the placenta, the prostate, the carotid artery, the thyroid, and the blood vessel, the tissue, the prostate, and the human body organs which allow the ultrasound examination using Doppler effects.

FIG. 3 illustrates an embodiment of an organ edge width enlarger 48b for generating an edge component 122 having an enlarged width by enlarging the width of an edge component 520 detected by the organ edge detector 48a in a two-dimensional space. The organ edge width enlarger 48b includes a low pass filter 540 for obtaining a blurred edge component 521 from the detected edge component 520, and an edge determiner 541 for obtaining the edge component 122 having the enlarged width by setting a threshold for adjusting the enlargement width for the blurred edge component 521 and determining that only a value equal to or greater than the threshold as a value of the edge component.

In an example, the threshold for adjusting the edge enlargement width is provided from the edge width adjuster 541a.

The reference numeral 553a represents an organ edge image obtained in such a way that the organ label image on which the semantic segmentation artificial intelligence network 44 performs the semantic segmentation of the ultrasound image is applied to the organ edge detector 48a.

The reference numeral 553b represents an organ edge image including the edge component 122 in which the width of the edge component of the organ edge image 553a is enlarged by the organ edge width enlarger 48b.

FIG. 4 illustrates an embodiment of a process for searching and recognizing a position of the fetus on the ultrasound image. In the process, in order to detect the fetus inside the uterus serving as one of the interest organs from the ultrasound image, a semantic segmentation image 551 for the fetus is obtained by the semantic segmentation artificial intelligence network 44. Thereafter, an organ label image 552 including a fetal region 24a is obtained from a semantic segmentation image 551 by the interest organ label separator 46. Thereafter, an organ edge image 553a indicating an edge component of an organ label image 552 is obtained by the organ edge detector 48a. Thereafter, the edge overlapping quantity calculator 48c calculates the number of overlapping edge pixels overlapped by comparing the edge component on the organ edge image 553a and the edge component 121 on the ultrasound image with each other in a two-dimensional space.

The organ label image 552 is an image for separately displaying only the fetal region 24a serving as the interest organ.

The edge overlapping quantity calculator 48c compares the edge component on the organ edge image 553a and the edge component 121 on the ultrasound image with each other.

When the number of overlapping edge pixels overlapped on two-dimensional spatial coordinates reaches a predetermined number, it is determined that the fetus is present in the ultrasound image region corresponding to the fetal region 24a.

In a case where the interest organ presence determiner 42 determines that the number of overlapping edge pixels is smaller than a predetermined numeric value, the edge component on the organ edge image 553b in which the edge width of the organ edge image 553a is enlarged twice by the organ edge width enlarger 48b is used. In this manner, the presence or absence of the fetus is reconfirmed by comparing the edge component on the organ edge image 553b with the edge component 121 on the ultrasound image.

Desirably, according to another aspect of the present disclosure, the interest organ presence determiner 42 determines the presence or absence of the fetus by using a ratio occupied by the number of overlapping edge pixels between the edge component on the organ edge image and the edge component 121 on the ultrasound image, compared to the total number of edge pixels of the edge component on the organ edge image.

The reference numeral 551 illustrates an embodiment in which the image of the fetal region 24a on which the semantic segmentation is performed and which is obtained by the semantic segmentation artificial intelligence network 44 is superimposed on the ultrasound image for convenience.

FIG. 5 illustrates an embodiment in which the artificial intelligence ultrasound-medical-diagnosis apparatus 600 using the semantic segmentation according to the present disclosure is connected to an artificial intelligence virtual doctor 79 resident in a remote medical-diagnosis system 700 so as to automatically analyze and diagnose ultrasound medical image data.

According to an embodiment of the present disclosure, the remote medical-diagnosis system 700 may include ultrasound-medical equipment 60, a wireless transmitter 60a, a camera 61, a first authenticator 62, a recorder 63, an Internet connector 64, an artificial intelligence neural network 70, a guide member 71, a diagnosis member 72, the virtual doctor 79, a medical professional terminal 200, a user terminal 400, the ultrasound-medical-diagnosis apparatus 600, and a communication interface 602.

According to an embodiment of the present disclosure, the ultrasound-medical equipment 60 may include an ultrasound probe sensor.

In addition, the wireless transmitter 60a may be integrated into the ultrasound-medical equipment 60, and may wirelessly transmit medical image data of a patient which is measured by the ultrasound-medical equipment 60.

The artificial intelligence ultrasound-medical-diagnosis apparatus 600 may receive the ultrasound image of the patient which is transmitted from the wireless transmitter 60a, and may automatically rank the disease level.

In addition, the camera 61 may monitor a use status of the ultrasound-medical equipment 60.

In addition, the first authenticator 62 may wirelessly authenticate a product ID of the ultrasound-medical equipment 60.

In addition, the recorder 63 may store the ultrasound image of the patient which is obtained from the ultrasound-medical equipment 60.

In addition, the Internet connector 64 may transmit the ultrasound image and the product ID of the ultrasound-medical equipment 60 to a remote diagnosis server 203 through a communication network 202, and may provide a communication channel for a remote consulting service.

The user terminal 400 may include a first consulting servicer 65 that provides the consulting service exchanged with the medical professional.

In addition, the communication interface 602 may provide connection between the artificial intelligence ultrasound-medical-diagnosis apparatus 600 and the user terminal 400.

In addition, the artificial intelligence neural network 70 may be resident in a form of software on the user terminal 400, and may be subjected to deep learning by using medical image database accumulated by the ultrasound-medical equipment 60.

According to an embodiment of the present disclosure, the virtual doctor 79 may include the guide member 71 and the diagnosis member 72.

The guide member 71 may be resident in a form of software on the user terminal 400 so as to guide or instruct a method of using the ultrasound-medical equipment 60. The diagnosis member 72 may output a diagnosis result by causing the artificial intelligence neural network 70 subjected to deep learning in advance to automatically analyze the medical image data obtained from the patient by the ultrasound-medical equipment 60.

In addition, a receptor (not illustrated) may receive the medical image data or the ultrasound image through the communication network 202. The medical professional terminal 200 may include a second consulting servicer that provides a consulting service between the user and the medical professional.

The guide member 71 may cause the camera 61 to monitor a use status of the ultrasound-medical equipment 60 on a real-time basis so as to guide or instruct a method of using the ultrasound-medical equipment 60 for the user.

In an example, the medical professional terminal 200 includes a camera 14, microphone 15, and a mouse 11.

Desirably, the artificial intelligence neural network 70 is shared with the artificial intelligence neural network 54 inside the artificial intelligence ultrasound-medical-diagnosis apparatus 600 according to the present disclosure.

Hereinafter, an operation flow according to the present disclosure will be briefly described based on the contents described above in detail.

Although not illustrated in the drawings, a remote medical-diagnosis method using the artificial intelligence ultrasound-medical-diagnosis apparatus using the semantic segmentation may be performed by the above-described artificial intelligence ultrasound-medical-diagnosis apparatus 600 using the semantic segmentation. Therefore, hereinafter, even if the contents are omitted, the contents of the artificial intelligence ultrasound-medical-diagnosis apparatus 600 using the semantic segmentation are similarly applicable to the contents of the remote medical-diagnosis method using the artificial intelligence ultrasound-medical-diagnosis apparatus using the semantic segmentation.

In Step S101, the artificial intelligence ultrasound-medical-diagnosis apparatus 600 using the semantic segmentation may extract the edge component included on the ultrasound image.

In Step S102, the artificial intelligence ultrasound-medical-diagnosis apparatus 600 using the semantic segmentation may acquire a semantic segmentation image by causing the semantic segmentation artificial intelligence network to perform the semantic segmentation on the ultrasound image.

In Step S103, the artificial intelligence ultrasound-medical-diagnosis apparatus 600 using the semantic segmentation may form the organ label image by extracting the interest organ region from the semantic segmentation image.

In Step S104, the artificial intelligence ultrasound-medical-diagnosis apparatus 600 using the semantic segmentation may acquire the organ edge image indicating the edge component of the organ label image.

In Step S105, the artificial intelligence ultrasound-medical-diagnosis apparatus 600 using the semantic segmentation may compare the edge component on the organ edge image and the edge component on the ultrasound image with each other on the two-dimensional spatial coordinates, and may recognize a position of the interest organ on the ultrasound image by calculating the number of overlapping edge pixels.

In Step S106, the artificial intelligence ultrasound-medical-diagnosis apparatus 600 using the semantic segmentation may include a whole medically associated ultrasound-medical-diagnosis interest region around the region of interest, on the interest region image.

In Step S107, the artificial intelligence ultrasound-medical-diagnosis apparatus 600 using the semantic segmentation may output a diagnosis result to the user terminal in such a way that the artificial intelligence neural network subjected to deep learning in advance with the interest region image by the virtual doctor automatically analyzes the interest region image.

In Step S108, the artificial intelligence ultrasound-medical-diagnosis apparatus 600 using the semantic segmentation may use the diagnosis result to perform the remote consulting service exchanged with the medical professional.

In the above description, Steps S101 to S108 may be further divided into additional steps, or may be combined into fewer steps, depending on the embodiment of the present disclosure. In addition, some steps may be omitted if necessary, and the order between the steps may be changed.

The remote medical-diagnosis method using the artificial intelligence ultrasound-medical-diagnosis apparatus using the semantic segmentation according to an embodiment of the present disclosure may be implemented in a form of program instructions that can be executed through various computer means, and may be recorded on a computer-readable medium. The computer-readable medium may include program instructions, data files, or data structures alone or in combination with each other. The program instructions recorded on the medium may be specially designed and configured for the present disclosure, or may be known and available to those skilled in computer software. Examples of computer-readable recording media include magnetic media such as hard disks, floppy disks, and magnetic tapes, optical media such as CD-ROMs and DVDs, magneto-optical media such as floptical disks, and hardware devices specifically configured to store and execute program instructions such as a ROM, a RAM, and a flash memory. Examples of the program instructions include not only machine language codes produced by a compiler, but also high-level language codes that can be executed by a computer using an interpreter. The hardware devices described above may be operated as one or more software modules to perform the operations according to the present disclosure, and vice versa.

In addition, the remote medical-diagnosis method using the artificial intelligence ultrasound-medical-diagnosis apparatus using the above-described semantic segmentation may also be implemented in a form of a computer program or an application executed by a computer stored in a recording medium.

The present disclosure has been described as an example, and those ordinarily skilled in the technical field of the present disclosure may understand that the present disclosure can easily be modified to other specific forms without changing the technical idea or essential characteristics of the present disclosure. Therefore, it should be understood that the embodiments described above are illustrative in all respects and not restrictive. For example, each component described as a single type may be realized in a distributed manner, and similarly, components described in a distributed manner may be realized in a combined form.

The artificial intelligence ultrasound-medical-diagnosis apparatus 600, the ultrasound probe sensor 30, the ultrasound image edge detector 32, the standard organ ultrasound image database 36, the interest region image database 37, the interest organ presence determiner 42, the examination item selection button inputter 43, the semantic segmentation artificial intelligence network 44, the interest organ label separator 46, the interest organ searcher 48, the interest region image extractor 50, the artificial intelligence neural network 54, the disease level displayer, and the wireless message transmitter 55 in FIG. 1-5 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-5 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An ultrasound-medical-diagnosis apparatus using semantic segmentation, comprising:
   an ultrasound probe sensor configured to acquire an ultrasound image from a patient;
   an ultrasound image edge detector configured to detect a plurality of edge components on the ultrasound image;
   an ultrasound examination item selection button inputter configured to receive an input from a user to select an organ of interest to examine;
   a semantic segmentation artificial intelligence network configured to perform labeling on each of a plurality of organs of the patient by using mutually different colors to detect a position of the organ of interest on the ultrasound image;
   an interest organ label separator configured to generate an organ label image displayed by extracting and separating the organ of interest selected by the user from the plurality of organs;
   an interest organ searcher comprising an organ edge detector configured to generate an organ edge image by detecting an edge component of the organ label image derived from a two-dimensional image of the organ of interest, an organ edge width enlarger configured to generate an organ edge image with enlarged edge width by enlarging an edge width of the edge component detected by the organ edge detector such that the edge component enlarges in a greater proportion than rest of the organ of interest, and an edge overlapping quantity calculator configured to calculate a number of overlapping edge pixels by comparing the edge component on the organ edge image and the edge component of the two-dimensional image with each other on two-dimensional spatial coordinates;
   an interest organ presence determiner configured to determine whether the organ of interest is present at each pixel of the two-dimensional image using the number of overlapping edge pixels calculated by the edge overlapping quantity calculator;
   an interest region image extractor configured to extract an interest region image from the two-dimensional image through space addressing on the ultrasound image for an organ of interest region or an ultrasound-medical-diagnosis interest region around the organ of interest region, upon the organ of interest being present on the ultrasound image; and
   a disease level displayer configured to determine and display a disease type and a disease level of the organ of interest based on the interest region image.

2. The apparatus of claim 1, wherein the semantic segmentation artificial intelligence network is deep-learning trained in advance based on a standard organ ultrasound image database including a labeled standard organ ultrasound image.

3. The apparatus of claim 1, further comprising an interest region image database including ultrasound images that are each labeled with disease type and disease level for organs inside a human body.

4. The apparatus of claim 1, further comprising a wireless message transmitter configured to transmit the disease level information to a mobile device of the patient in a form of a wireless message.

5. The apparatus of claim 1, wherein the interest organ presence determiner further includes an edge width adjuster configured to transmit a feedback signal for enlarging the edge width to the organ edge width enlarger.

6. The apparatus of claim 1, wherein the semantic segmentation artificial intelligence network comprises:
   an artificial intelligence neural network configured to perform semantic segmentation based on learning that is performed in advance based on a plurality of ultrasound images,
   wherein the semantic segmentation to be performed involves at least one examination selected from the group consisting of a fetal examination, a carotid artery examination, a breast examination, an appendix examination, a prostate ultrasound examination, a thyroid examination, a vascular Doppler ultrasound examination, and an organ-based ultrasound examination based on at least one organ or a part of an organ selected from the group consisting of a liver, a heart, a joint, a spine, a uterus, a gallbladder, a genital, a bile duct, a pancreas, a spleen, a kidney, or a combination thereof.

7. The apparatus of claim 4, wherein the method of using the ultrasound-medical equipment comprises:
   extracting an edge component of an ultrasound image;
   acquiring a semantic segmentation image by using the semantic segmentation artificial intelligence network to perform semantic segmentation on the ultrasound image;
   forming an organ label image by extracting an interest organ region from the semantic segmentation image;
   causing an organ edge detector to acquire an organ edge image indicating an edge component;
   comparing the edge component on the organ edge image and the edge component on the ultrasound image with each other on two-dimensional spatial coordinates, and recognizing a position of an interest organ on the ultrasound image by calculating the number of overlapping edge pixels;
   including an ultrasound-medical-diagnosis interest region around the extracted organ of interest region, on an interest region image;
   outputting a diagnosis result by using the artificial intelligence neural network that performed deep learning in advance in order to automatically analyze the interest region image; and
   performing a remote consulting service with a medical professional, based on the diagnosis result.

8. The apparatus of claim 4, wherein the ultrasound examination item selection button inputter is configured to receive the input from the user via a touch screen that allows the user to select an organ.

9. An ultrasound-medical-diagnosis apparatus, comprising:
   an ultrasound probe sensor configured to acquire an ultrasound image;
   an ultrasound image edge detector configured to detect edge components on the ultrasound image;
   an ultrasound examination item selection button inputter configured to receive an input from a user via a touch screen to select an organ of interest to be examined by the apparatus;

a semantic segmentation artificial intelligence network configured to label organs present on the ultrasound image;
an interest organ label separator configured to extract and separate the organ of interest selected by the user from other organs shown on the ultrasound image;
an interest organ searcher configured to:
  detect an edge component of the organ of interest; and
  generate an organ edge image by enlarging a width of the edge component in a greater proportion than other portions of the selected organ of interest, the width being uniformly enlarged along the edge component based on an edge width enlargement ratio;
an interest region image extractor configured to, in response to the organ of interest being present on the ultrasound image, extract an interest region that includes the organ of interest from the ultrasound image; and
a disease level displayer configured to display a disease type and a disease level of the organ of interest based on the interest region image.

10. The apparatus of claim 9, wherein the semantic segmentation artificial intelligence network is a deep-learning neural network that is trained on a plurality of ultrasound images associated with disease types and disease levels.

11. The apparatus of claim 1, wherein the organ edge width enlarger is configured to enlarge the edge width based on an edge width enlargement ratio, the edge width enlargement ratio being a numerical value.

12. The apparatus of claim 1, wherein the organ edge width enlarger is configured to enlarge the edge width uniformly along the edge component based on an edge width enlargement ratio.

13. The apparatus of claim 9, wherein the edge width enlargement ratio is a numerical value.

* * * * *